US012767933B2

(12) United States Patent
Chung et al.

(10) Patent No.: US 12,767,933 B2
(45) Date of Patent: Oct. 20, 2026

(54) METHOD OF CULTURING RECONSTRUCTED HUMAN SKIN

(71) Applicant: Korea University Research and Business Foundation, Seoul (KR)

(72) Inventors: Seok Chung, Seoul (KR); Jihee Won, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 591 days.

(21) Appl. No.: 17/957,166

(22) Filed: Sep. 30, 2022

(65) Prior Publication Data

US 2023/0095689 A1 Mar. 30, 2023

(30) Foreign Application Priority Data

Sep. 30, 2021 (KR) ........................ 10-2021-0129433
Aug. 25, 2022 (KR) ........................ 10-2022-0106664

(51) Int. Cl.
*C12N 5/071* (2010.01)
*C12M 3/00* (2006.01)

(52) U.S. Cl.
CPC ........... *C12N 5/0698* (2013.01); *C12M 21/08* (2013.01); *C12N 2533/32* (2013.01); *C12N 2533/54* (2013.01)

(58) Field of Classification Search
None
See application file for complete search history.

(56) References Cited

U.S. PATENT DOCUMENTS

2019/0144821 A1 5/2019 Klaka et al.
2020/0405912 A1* 12/2020 Silva Barros ........... A61L 27/48

FOREIGN PATENT DOCUMENTS

| | | | | | |
|---|---|---|---|---|---|
| CN | 109082391 | A | * | 12/2018 | ............... C12N 1/16 |
| CN | 109321513 | | * | 2/2019 | ......... A61L 27/3804 |
| CN | 109321513 | A | * | 2/2019 | ............. A61L 27/60 |
| CN | 109082391 | B | * | 11/2020 | ............. A01N 63/00 |
| JP | 2020-202754 | A | | 12/2020 | |
| KR | 10-2019-0003060 | A | | 1/2019 | |
| KR | 10-2021-0095518 | A | | 8/2021 | |

OTHER PUBLICATIONS

Cascade Biologics, "Coating Matrix Kit", 2009, Invitrogen Cell Culture, Protocol (Year: 2009).*
Gibco, "Gibco Poly-D-Lysine", 2019, ThermoFisher Scientific, Protocol (Year: 2019).*

(Continued)

*Primary Examiner* — Tracy Vivlemore
*Assistant Examiner* — Hanna Maire Thueson
(74) *Attorney, Agent, or Firm* — NSIP Law

(57) ABSTRACT

Disclosed is a method of producing reconstructed human skin, and particularly a method of producing reconstructed human skin using a culture vessel including an inner chamber surrounded by an inner wall and a porous bottom surface and an outer chamber spaced apart from the inner chamber and configured to surround the inner chamber, including forming an adhesive layer by coating the inner wall with an adhesive material and culturing reconstructed human skin in the culture vessel having the adhesive layer formed thereon.

7 Claims, 10 Drawing Sheets

(56) References Cited

OTHER PUBLICATIONS

Thermo Scientific, "Establishing human skin tissue on Nunc Cell Culture Inserts in Carrier Plate Systems", 2018, Thermo Scientific, Protocol (Year: 2018).*
LKT Laboratories, Inc, "Dopamine Hydrochloride", 2020, LKT Laboratories Inc., MSDS (Year: 2020).*
English translation of Wen et al. 2025.*
Xu et al., Polydopamine-induced hydroxyapatite coating facilitates hydroxyapatite/polyamide 66 implant osteogenesis: an in vitro and in vivo evaluation, 2018, International Journal of Nanomedicine, vol. 13, p. 8179-8193 (Year: 2018).*
Thermofisher (Thermo scientific), Establishing human skin tissue on Nunc Cell Culture Inserts in Carrier Plate Systems, 2018, Thermofisher, p. 1-4 (Year: 2018).*
Sarrigiannidis et al., A tough act to follow: collagen hydrogel modifications to improve mechanical and growth factor loading capabilities, 2021, Materials Today Bio, vol. 10, p. 1-22 (Year: 2021).*
Lee, Vivian, et al. "Design and fabrication of human skin by three-dimensional bioprinting." Tissue Engineering Part C: Methods 20.6 (2014): 473-484.
Bouwstra, Joke A., et al., "Human skin equivalents: Impaired barrier function in relation to the lipid and protein properties of the stratum corneum." Advanced Drug Delivery Reviews 175 (2021): 113802.
Korean Office Action issued on Dec. 19, 2024, in counterpart Korean Patent Application No. 10-2022-0106664 (4 pages in English, 4 pages in Korean).
Extended European search report issued on Feb. 16, 2023, in counterpart European Patent Application No. 22198764.7 (8 pages in English).
Korean Notice of Allowance issued on Nov. 7, 2025, in counterpart Korean Patent Application No. 10-2022-0106664. (2 pages in English, 2 pages in Korean).

* cited by examiner

[FIG. 1]
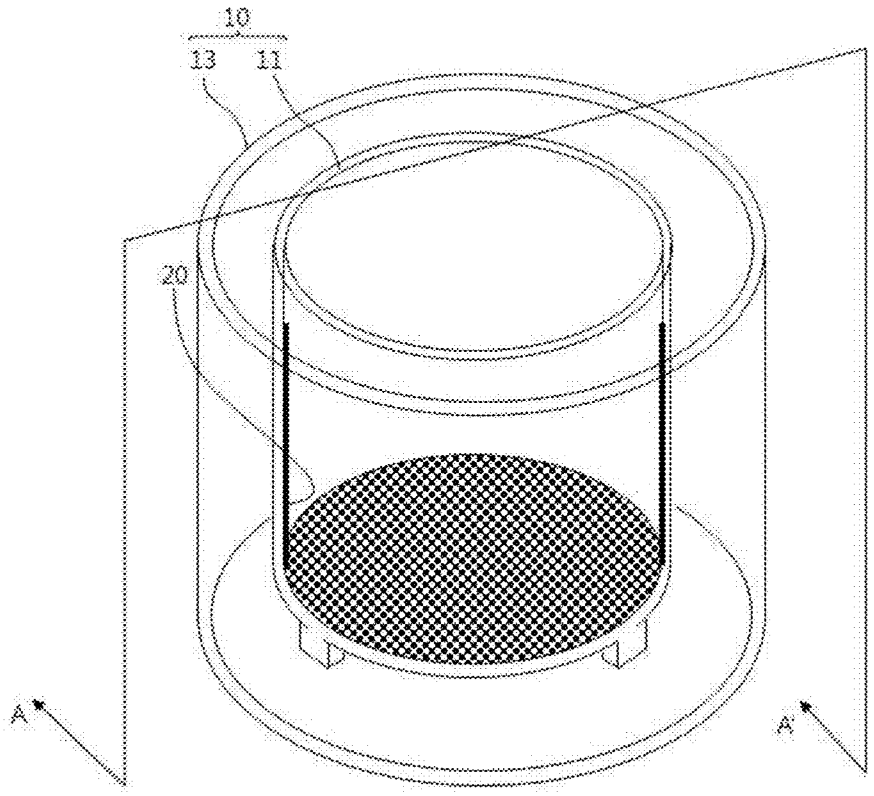

[FIG. 2]
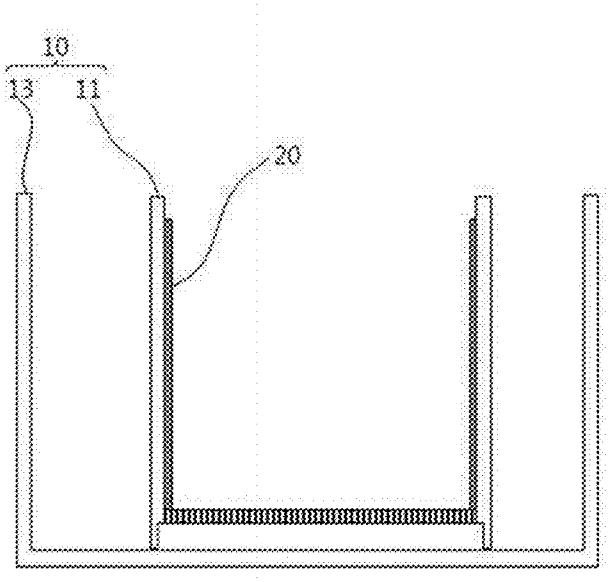

[FIG. 3]
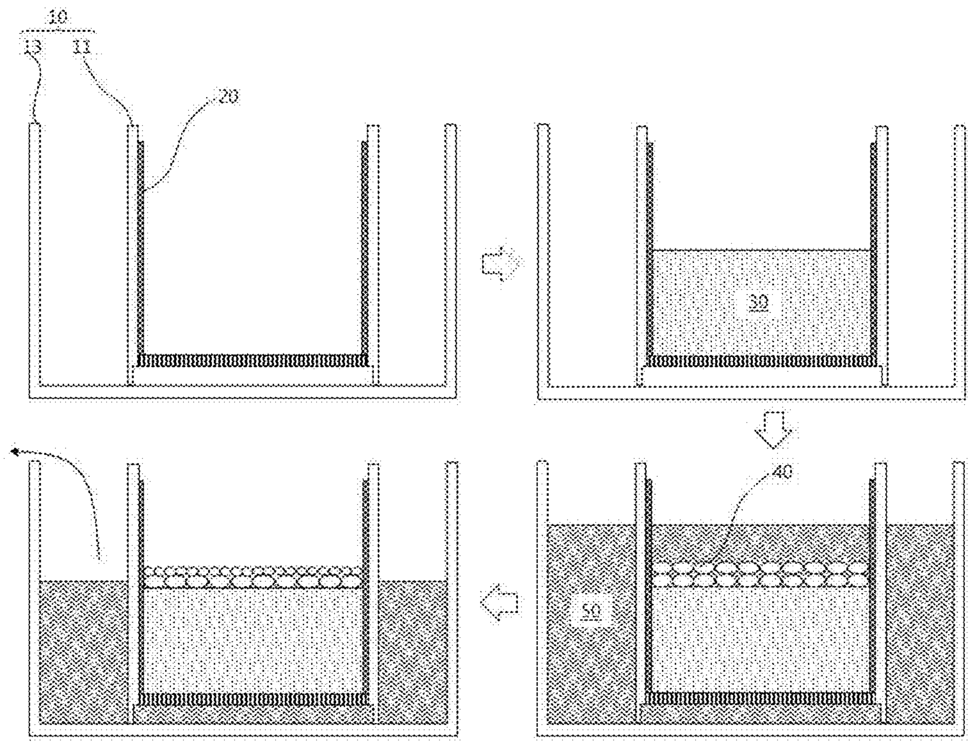

[FIG. 4A]
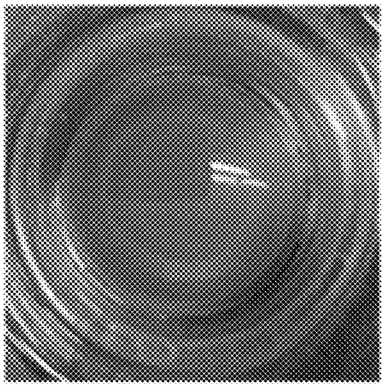
[FIG. 4B]
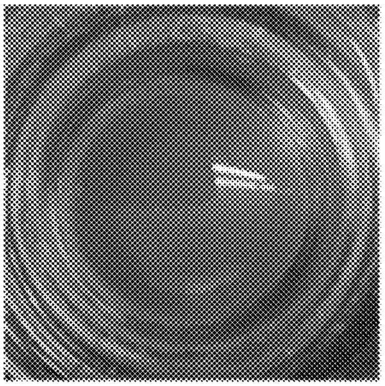

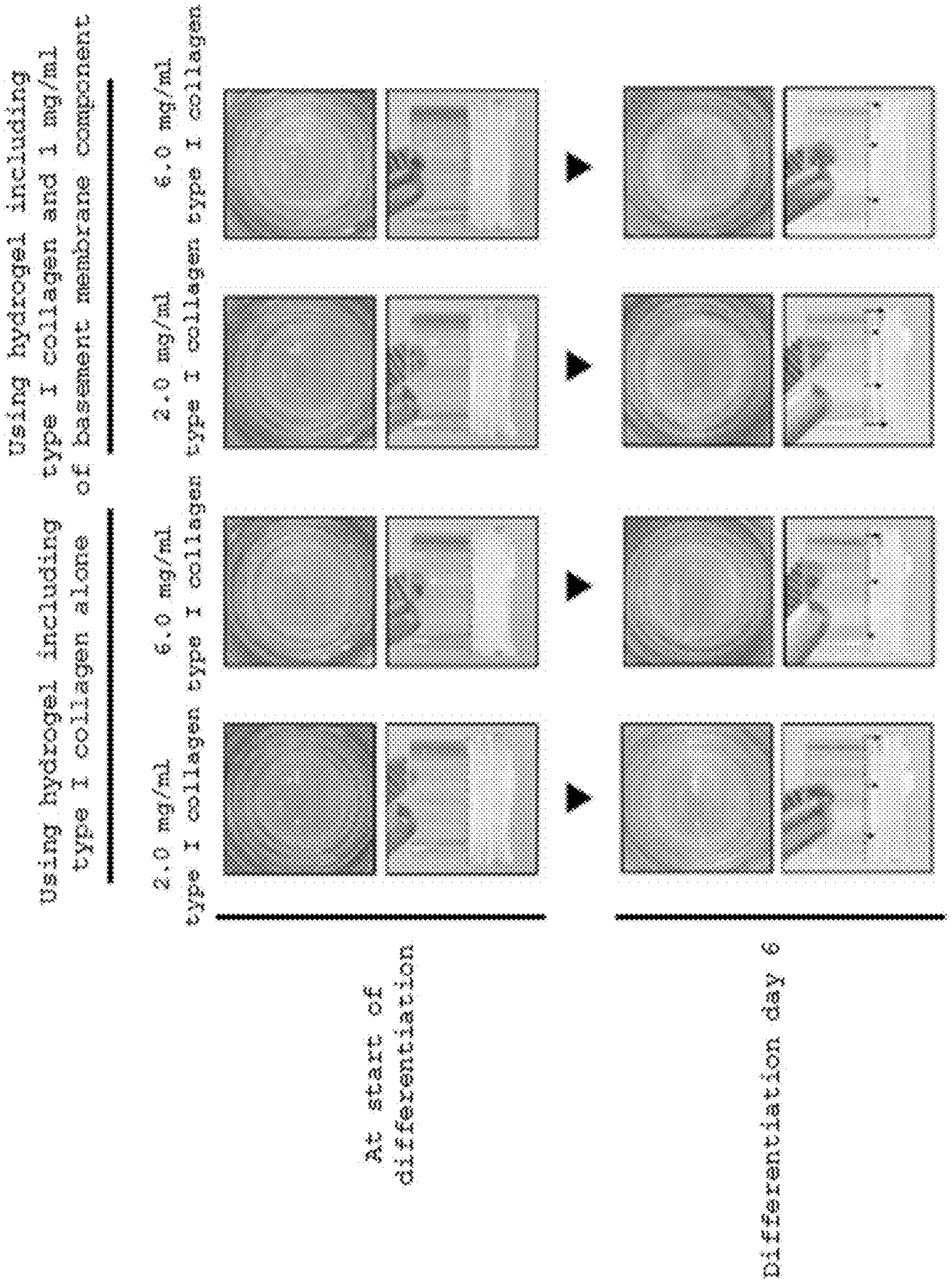
[FIG. 5A]

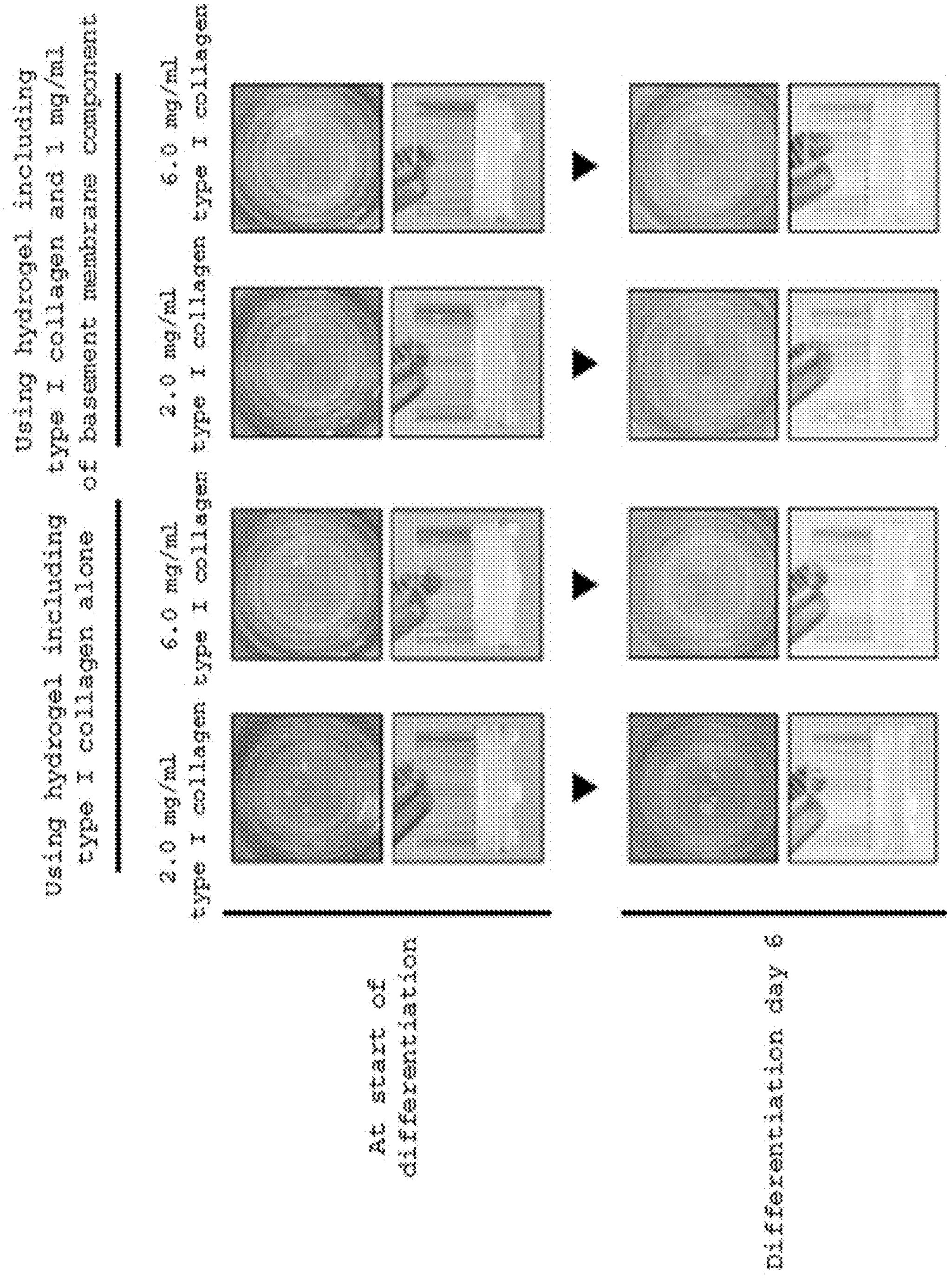
[FIG. 5B]

[FIG. 6A]
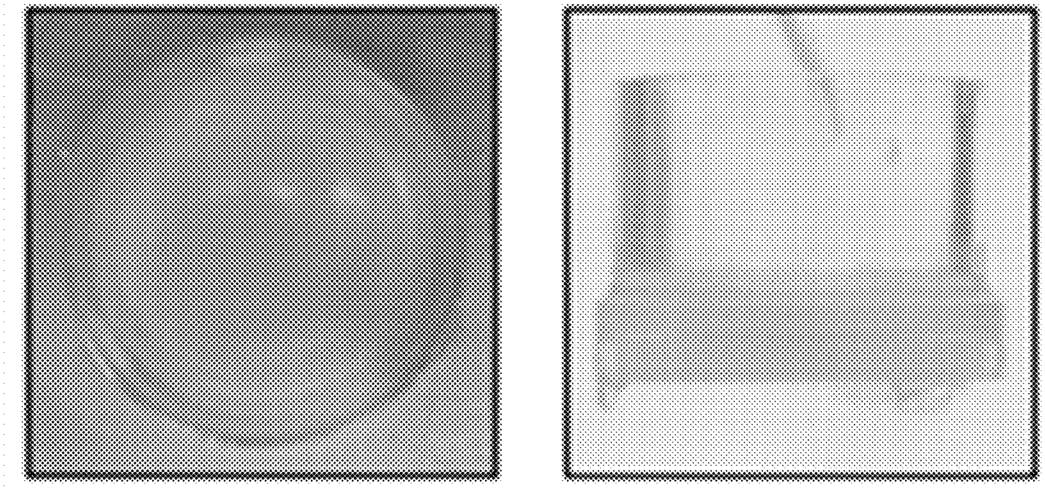

[FIG. 6B]
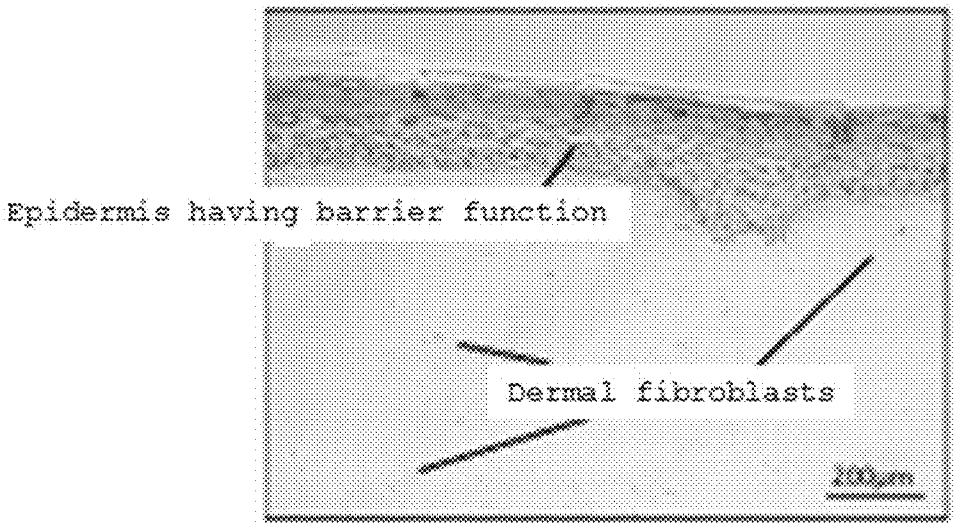

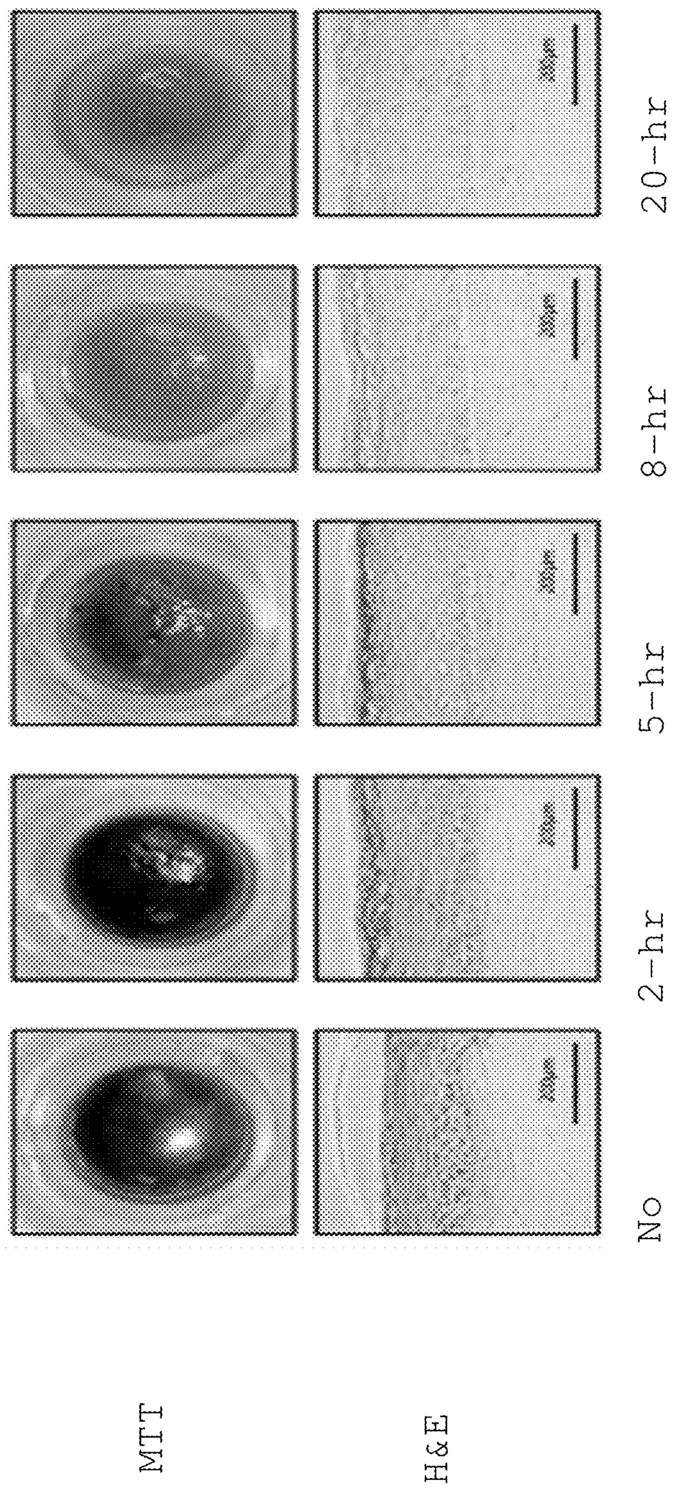
[FIG. 7]

[FIG. 8]
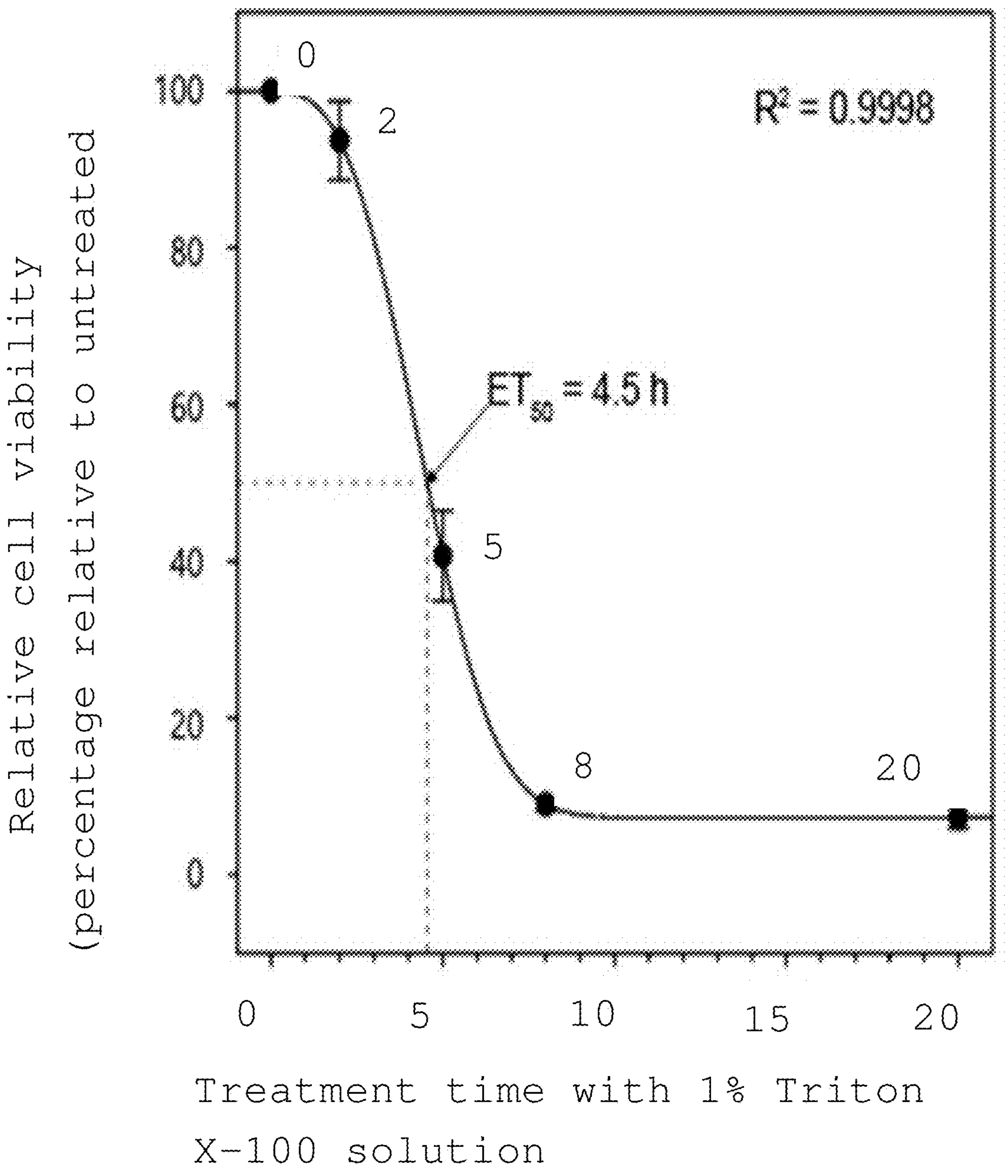

METHOD OF CULTURING RECONSTRUCTED HUMAN SKIN

CROSS-REFERENCE TO RELATED APPLICATIONS

This application claims the benefit under 35 USC § 119(a) of Korean Patent Application No. 10-2021-0129433 filed on Sep. 30, 2021 and Korean Patent Application No. 10-2022-0106664 filed on Aug. 25, 2022 in the Korean Intellectual Property Office, the entire disclosures of which are incorporated herein by reference for all purposes.

BACKGROUND OF THE INVENTION

Field of the Invention

The present invention relates to a method of culturing reconstructed human skin composed of a dermis and an epidermis, and more particularly to a method of culturing reconstructed human skin, which is capable of culturing reconstructed human skin that does not contract so as to enable the barrier function thereof to be evaluated through treatment of a liquid material on the upper portion thereof by preventing reconstructed human skin from being deformed during culture.

Description of the Related Art

The skin is a large organ that surrounds the body, and is broadly divided into two layers, namely the epidermis and dermis, from the outermost surface thereof. The epidermis is mostly composed of epidermal keratinocytes, which form a layered structure, and the dermis contains blood vessels, nerves, sebaceous glands, and the like based on a matrix including dermal fibroblasts inside matrix proteins such as collagen fibers and elastic fibers. In the skin, the barrier function of the epidermis is regarded as the most important, and the skin barrier function protects the body by blocking penetration of external pollutants and irritants and prevents loss of body fluids by blocking evaporation of moisture inside the body.

Reconstructed human skin (RhS) is a skin equivalent produced in a manner in which a dermis equivalent composed of a type-I-collagen-based three-dimensional hydrogel scaffold matrix including dermal fibroblasts is placed in a special culture vessel (a filter membrane insert), the bottom surface of which is formed of a porous membrane, epidermal keratinocytes are applied thereon, and the upper portion thereof is exposed to air to induce differentiation of the epidermal keratinocytes, thereby forming a mature reconstructed epidermis having a skin barrier function. This reconstructed human skin is used to replace damaged parts of the skin such as burns, external injuries, etc., or is used in skin physiology research, evaluation of skin irritation of specific materials, or evaluation of functional improvement efficacy thereof.

However, reconstructed human skin is detached from the inner wall of the culture vessel due to continuous internal tension generated by dermal fibroblasts contained in the dermis equivalent during culture and temporary contractile force generated by the migratory epidermal keratinocytes during differentiation thereof, and thus contraction with a gradual decrease in volume occurs, and a part of the bottom surface of the culture vessel is exposed. In an experiment using the reconstructed human skin with contraction including treatment of a liquid material on the upper portion thereof, thus the liquid material is mostly mixed with the culture medium through the exposed porous membrane and delivered directly to the dermis, and as such, there is a limitation in that only experiments neglecting the barrier function of the epidermis, which is the most important functional property of the skin, are possible.

SUMMARY OF THE INVENTION

The present invention has been made keeping in mind the problems encountered in the related art, and an object of the present invention is to provide a method of coating the inner wall of a culture vessel in order to prevent detachment of reconstructed human skin, which is the starting point of contraction of reconstructed human skin when producing reconstructed human skin, and reconstructed human skin produced without contraction using the same and configured such that an epidermis having a skin barrier function is formed on a dermis equivalent matrix, in which the skin barrier function may be reflected in an experiment including treatment of a liquid material on the upper portion thereof and delivery of the liquid material into the dermis thereof.

An embodiment of the present invention provides a method of producing reconstructed human skin using a culture vessel including an inner chamber surrounded by an inner wall and a porous bottom surface and an outer chamber spaced apart from the inner chamber and configured to surround the inner chamber, including (a) forming an adhesive layer by coating the inner wall with an adhesive material and (b) culturing reconstructed human skin in the culture vessel having the adhesive layer formed thereon.

Also, in the method according to an embodiment of the present invention, the adhesive material may be any one of dopamine and poly-d-lysine or a mixture thereof.

Also, in the method according to an embodiment of the present invention, step (a) may include preparing a coating solution by dissolving the adhesive material in a powder form in a solvent, and forming the adhesive layer by placing the coating solution in the inner chamber and carrying out reaction.

Also, in the method according to an embodiment of the present invention, the adhesive material may be dopamine at a concentration of 0.1 to 20 mg/ml.

Also, in the method according to an embodiment of the present invention, the solvent may be Tris-HCl at a pH of 8.0 to 9.0.

Also, in the method according to an embodiment of the present invention, the adhesive material may be poly-d-lysine at a concentration of 0.1 to 50 mg/ml.

Also, in the method according to an embodiment of the present invention, step (b) may include forming a three-dimensional hydrogel scaffold matrix by placing a scaffold solution including a type I collagen solution in the inner chamber and performing gelling, and seeding epidermal keratinocytes onto the three-dimensional hydrogel scaffold matrix.

Also, in the method according to an embodiment of the present invention, the scaffold solution may further include dermal fibroblasts.

Also, in the method according to an embodiment of the present invention, the scaffold solution may further include a basement membrane component material.

Also, in the method according to an embodiment of the present invention, seeding the epidermal keratinocytes may include supplying a first culture medium including the epidermal keratinocytes to the inner chamber.

Also, the method according to an embodiment of the present invention may further include supplying a first culture medium to the inner chamber and the outer chamber so that the epidermal keratinocytes are attached, after seeding the epidermal keratinocytes.

Also, the method according to an embodiment of the present invention may further include removing the first culture medium and supplying a second culture medium to the outer chamber so that the epidermal keratinocytes differentiate.

The features and advantages of the present invention will become more apparent from the following detailed description taken in conjunction with the accompanying drawings.

The terms or words used in the present specification and the claims should not be interpreted as being limited merely to the ordinary and dictionary meanings, but should be interpreted based on the meanings and concepts of the invention in keeping with the scope of the invention based on the principle that the inventors can appropriately define the terms in order to describe the invention in the best way.

BRIEF DESCRIPTION OF THE DRAWINGS

FIG. 1 is a perspective view showing a culture vessel used in a process of producing reconstructed human skin according to the present invention;

FIG. 2 is a cross-sectional view taken along line A-A' of FIG. 1;

FIG. 3 is a flowchart showing the process of producing reconstructed human skin according to the present invention;

FIG. 4A is a photographic image showing a dermis equivalent completed according to Comparative Example 1;

FIG. 4B is a photographic image showing a dermis equivalent completed according to Example 1;

FIG. 5A is photographic images showing an epidermis obtained by differentiating epidermal keratinocytes on a type-I-collagen-based three-dimensional hydrogel scaffold matrix according to Comparative Example 1;

FIG. 5B is photographic images showing an epidermis obtained by differentiation of epidermal keratinocytes on a type-I-collagen-based three-dimensional hydrogel scaffold matrix according to Example 1;

FIG. 6A is images showing the reconstructed human skin produced according to Example 1;

FIG. 6B is an optical microscope image showing a cross-section of the reconstructed human skin produced according to Example 1 stained with hematoxylin and eosin (H&E);

FIG. 7 is photographic images showing a thiazolyl blue formazan dye formed through reaction of 1 mg/ml of an MTT solution with viable cells for 3 hours following topical application of 200 μL of a 1% Triton X-100 solution on the upper surface of the reconstructed human skin produced according to Example 1 and incubation for 2 hours, 5 hours, 8 hours, and 20 hours, along with an untreated control, and optical microscope images showing the histology of the reconstructed human skin stained with hematoxylin and eosin (H&E) depending on the treatment time; and FIG. 8 is a graph showing relative cell viability determined by dissolving the formed formazan dye in 2 ml of 2-propanol, placing 200 μl thereof in each of two wells of a 96-well plate, and measuring and comparing optical density at a wavelength of 570 nm using a plate reader, and showing $ET_{50}$ (Effective Time 50), which is the time taken to reach the cell viability of 50%.

DETAILED DESCRIPTION OF THE INVENTION

The objects, specific advantages, and novel features of the present invention will become more apparent from the following detailed description taken in conjunction with the accompanying drawings and preferred embodiments. In the present specification, in adding reference numerals to the elements in drawings, it should be noted that the same reference numerals refer to the same elements throughout different drawings. Also, terms such as “first”, “second”, and the like are used to distinguish one element from another element, and the elements are not limited by these terms. Hereinafter, in describing the present invention, a detailed description of related known technology that may unnecessarily obscure the gist of the present invention will be omitted.

Hereinafter, a detailed description will be given of preferred embodiments of the present invention with reference to the accompanying drawings.

FIG. 1 is a perspective view showing a culture vessel 10 used in a process of producing reconstructed human skin according to the present invention, FIG. 2 is a cross-sectional view taken along line A-A' of FIG. 1, and FIG. 3 is a flowchart showing the process of producing reconstructed human skin according to the present invention.

As shown in FIGS. 1 to 3, the method of producing reconstructed human skin according to the present invention using a culture vessel 10 including an inner chamber 11 surrounded by an inner wall and a porous bottom surface and an outer chamber 13 spaced apart from the inner chamber 11 and configured to surround the inner chamber 11 includes forming an adhesive layer 20 by coating the inner wall with an adhesive material and culturing reconstructed human skin in the culture vessel 10 having the adhesive layer 20 formed thereon.

The present invention pertains to a method of producing reconstructed human skin by culturing reconstructed human skin. Here, reconstructed human skin narrowly means a skin equivalent in which an epidermis is formed on a three-dimensional hydrogel scaffold matrix based on type I collagen, which is a dermal component, and including dermal fibroblasts, and should be interpreted in the broadest sense, including all polymer composites that exhibit structural and functional properties similar to those of real skin. For example, even when the three-dimensional hydrogel scaffold matrix does not include dermal fibroblasts or includes a basement membrane component, the resulting product may correspond to reconstructed human skin.

This reconstructed human skin is cultured in a culture vessel 10, and the culture vessel 10 may be formed in a double-walled structure in which the inner chamber 11 is surrounded by the outer chamber 13. Here, the inner chamber 11 has an inner space formed by an inner wall and a bottom surface, the bottom surface may be made of a porous membrane having numerous micropores, and reconstructed human skin is cultured in the inner space. The outer chamber 13 has an outer wall and a bottom surface, and is spaced apart from the inner chamber 11 and is configured to surround the inner chamber 11.

The method of producing reconstructed human skin using the culture vessel 10 according to the present invention includes forming an adhesive layer and culturing reconstructed human skin.

In the formation of the adhesive layer, the inner wall of the inner chamber 11 is coated with an adhesive material, whereby the adhesive layer 20 is formed on the inner wall.

The adhesive material that is used may be any one of dopamine and poly-d-lysine or a mixture thereof. Dopamine is a material composed of 3,4-dihydroxy-L-phenylalanine (DOPA) and amine (lysine) groups, which are the main components that provide strong adhesion of Plaque secreted by *Mytilus edulis* to attach to rocks, and has a structure represented by Chemical Formula 1 below.

[Chemical Formula 1]

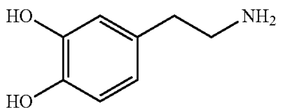

For example, a coating solution is prepared by dissolving an adhesive material in a powder form in a predetermined solvent, after which the coating solution is placed in the inner chamber 11 and allowed to react for a certain period of time, thereby forming an adhesive layer 20 on the surface of the inner wall of the inner chamber 11. More specifically, the adhesive layer 20 may be formed in a manner in which dopamine in a powder form is dissolved at a concentration of 0.1 to 20 mg/ml in Tris-HCl at a pH of 8.0 to 9.0 to afford a coating solution, which is then placed in the inner chamber 11 and allowed to react for 1 to 3 hours. Here, the solvent is not necessarily limited to Tris-HCl, the concentration of dopamine is not limited to the above range, or the reaction time is not limited to the above range. Moreover, the inner wall surface of the inner chamber 11 may be coated using a mixed solution of poly-d-lysine at a concentration of 0.1 to 50 mg/ml.

This adhesive layer 20 provides adhesion between the inner wall of the inner chamber 11 and a three-dimensional hydrogel scaffold matrix 30 to be described later.

In the culturing of the reconstructed human skin, reconstructed human skin is cultured in the culture vessel 10 having the adhesive layer 20 formed thereon. Here, a three-dimensional hydrogel scaffold matrix 30 is formed, and epidermal keratinocytes 40 are seeded onto the three-dimensional hydrogel scaffold matrix 30.

In order to form the three-dimensional hydrogel scaffold matrix 30, a scaffold solution including a type I collagen solution is placed in the inner chamber 11 and gelled. The scaffold solution may include type I collagen at a concentration of 2.0 to 6.0 mg/ml, but the concentration thereof is not necessarily limited thereto. Also, the scaffold solution may further include dermal fibroblasts, and as such, the three-dimensional hydrogel scaffold matrix 30 may be produced into a dermis equivalent. Here, the number of dermal fibroblasts may be $1.0\times10^5$ to $3.0\times10^5$ cells/ml, but is not necessarily limited thereto. Also, the scaffold solution may further include a basement membrane component material. The basement membrane component material may be at least one selected from the group consisting of laminin, type IV collagen, and type VII collagen, and the concentration thereof may be 0.1 to 50 mg/ml, but the type and concentration of the component material are not necessarily limited thereto.

Thereafter, epidermal keratinocytes 40 are seeded onto the three-dimensional hydrogel scaffold matrix 30 thus formed. Here, the number of epidermal keratinocytes 40 may be 100,000 to 400,000 cells/cm$^2$, but may be adjusted. Specifically, a first culture medium 50 including the epidermal keratinocytes 40 is supplied to the inner chamber 11 and a first culture medium 50 not including the epidermal keratinocytes 40 is supplied to the outer chamber 13, and after incubation time (e.g. 12 to 24 hours), the epidermal keratinocytes 40 may be attached. Alternatively, after seeding the epidermal keratinocytes 40, the first culture medium 50 may be further supplied to the inner chamber 11 and the outer chamber 13 so that the epidermal keratinocytes 40 are attached.

When the epidermal keratinocytes 40 are introduced in this way, differentiation thereof may be induced to form an epidermis. In order to form an epidermis having a skin barrier function in reconstructed human skin, the culture medium may be removed from the culture vessel 10 into which the epidermal keratinocytes 40 are introduced, the epidermal keratinocytes 40 may be exposed to air, and differentiation thereof may be induced. For example, the first culture medium 50 may be removed from the culture vessel 10, and a second culture medium for differentiation of the epidermal keratinocytes 40 may be supplied to the outer chamber 13. Thereafter, differentiation may be induced for 10 days while periodically replacing the culture medium. However, the period of time for inducing differentiation is not necessarily limited to 10 days.

A better understanding of the present invention may be obtained through the following examples and experimental examples.

Example 1: Manufacture of Culture Vessel Having Inner Wall Coated with Dopamine As an example of the present invention, a culture vessel having a coated inner wall was prepared in a manner in which a solution obtained by dissolving dopamine in a powder form at a concentration of 2.0 mg/ml in a Tris-HCl solvent at a pH of 8.5 was placed in a culture vessel (a filter membrane insert) having an outer diameter of 12 mm and having a porous bottom membrane, followed by reaction at room temperature for 2 hours.

Comparative Example 1

As a comparative example of the present invention, a culture vessel of the same type without any treatment was prepared.

Experimental Example 1: Culture of Dermis Equivalent

Using the culture vessel prepared in each of Example 1 and Comparative Example 1, a dermis equivalent was cultured through the following method. As such, the dermis equivalent was formed using a type-I-collagen-based three-dimensional scaffold including dermal fibroblasts (Normal Human Dermal Fibroblasts, LONZA).

Specifically, in order to prepare a type I collagen solution in 1×PBS (phosphate-buffered saline) at a pH of 7.6, a collagen-fibroblast-mixed solution having 2.0 mg/ml of type I collagen and $3.0\times10^5$ cells/ml of dermal fibroblasts was prepared by mixing type I collagen (Corning) with 10×PBS, 1.0 M NaOH, distilled deionized water (DDW), and a cell suspension including dermal fibroblasts in an appropriate ratio.

150 μl of the solution thus prepared was placed in each of Example 1 and Comparative Example 1, and stored for 30 minutes in an incubator at 37° C. and 5% $CO_2$ and thus gelled.

The culture vessel for culturing reconstructed human skin was placed in a chamber, after which a culture medium (Fibroblast Growth Medium-2, LONZA) was supplied to the chamber, followed by three-dimensional culture for 11 days.

The extent of contraction of the dermis was observed during culture of the dermis equivalent as described above, and the finally completed dermis equivalent was photographed. The results thereof are shown in FIGS. 4A and 4B. FIG. 4A is a photographic image showing the dermis equivalent completed according to Comparative Example 1, and FIG. 4B is a photographic image showing the dermis equivalent completed according to Example 1.

Consequently, in Comparative Example 1, which was the culture vessel without any treatment as shown in FIG. 4A, it was confirmed that the dermis equivalent was detached from the inner wall of the culture vessel and contracted due to the internal tension generated by the dermal fibroblasts contained in the dermis equivalent. In contrast, with reference to FIG. 4B using the culture vessel having the inner wall coated with dopamine in Example 1 according to the present invention, it was confirmed that, due to strong adhesion between the inner wall of the culture vessel and the type-I-collagen-based three-dimensional hydrogel scaffold corresponding to the matrix of the dermis equivalent, the dermis equivalent was not detached from the inner wall of the culture vessel, and thus, no contraction of the dermis equivalent occurred.

Experimental Example 2: Culture of Reconstructed Epidermis

Using the culture vessel prepared in each of Example 1 and Comparative Example 1, a reconstructed epidermis was cultured through the following method. This reconstructed epidermis was an epidermis having a skin barrier function obtained by culturing epidermal keratinocytes on a type-I-collagen-based three-dimensional scaffold matrix not including dermal fibroblasts (acellular dermal matrix) and inducing differentiation thereof.

Specifically, in order to prepare a type I collagen solution in 1×PBS at a pH of 7.6, 2.0 mg/ml to 6.0 mg/ml of a type I collagen solution was prepared by mixing type I collagen (Corning) with 10×PBS, 1.0 M NaOH, and DDW in an appropriate ratio, and 1.0 mg/ml of a basement membrane component was further added thereto to obtain a solution.

150 μl of each of the solutions thus obtained was placed in Example 1 and Comparative Example 1, and stored for 30 minutes in an incubator at 37° C. and 5% $CO_2$ and thus gelled.

Keratinocytes (Normal Human Epidermal Keratinocytes, LONZA) were seeded at 250,000 cells/$cm^2$ onto the type-I-collagen-based three-dimensional scaffold matrix not including dermal fibroblasts formed as described above, and a culture medium (Keratinocyte Growth Medium-GOLD, LONZA) was placed in the inner and outer chambers of the culture vessel, followed by cell attachment overnight. Thereafter, the culture medium was removed from the culture vessel, a culture medium for forming an epidermis was placed in the outer chamber, and differentiation of the keratinocytes was induced. Thereafter, the epidermis was produced by inducing differentiation for 10 days while changing the culture medium every day.

The extent of deformation of the three-dimensional hydrogel scaffold matrix was observed during culture of the reconstructed epidermis as described above, and the state after 6 days was photographed. The results thereof are shown in FIGS. 5A and 5B. FIG. 5A is photographic images showing the epidermis formed by inducing differentiation of epidermal keratinocytes on the type-I-collagen-based three-dimensional hydrogel scaffold matrix according to Comparative Example 1, and FIG. 5B is photographic images showing the epidermis formed by differentiating epidermal keratinocytes on the type-I-collagen-based three-dimensional hydrogel scaffold matrix according to Example 1.

Consequently, in Comparative Example 1, which was the culture vessel without any treatment as shown in FIG. 5A, it was confirmed that the three-dimensional hydrogel scaffold matrix was detached from the inner wall of the culture vessel due to contractile force generated by the migratory epidermal keratinocytes during differentiation thereof, and was thus deformed. In contrast, with reference to FIG. 5B, the culture vessel having the inner wall coated with dopamine in Example 1 according to the present invention created strong adhesion between the type-I-collagen-based three-dimensional hydrogel scaffold and the inner wall of the culture vessel, whereby the matrix was not detached from the inner wall of the culture vessel, confirming that almost no deformation occurred.

Experimental Example 3: Culture of Reconstructed Human Skin

Using the culture vessel prepared in Example 1, reconstructed human skin was cultured through the following method. This reconstructed human skin was produced by forming an epidermis having a skin barrier function by culturing epidermal keratinocytes on the dermis equivalent and inducing differentiation thereof.

Specifically, in order to prepare a type I collagen solution in 1×PBS (phosphate-buffered saline) at a pH of 7.6, a collagen-fibroblast-mixed solution including 6.0 mg/ml of type I collagen and $1.0\times10^5$ cells/ml of dermal fibroblasts was prepared by mixing type I collagen (Corning) with 10×PBS, 1.0 M NaOH, DDW (distilled deionized water), and a cell suspension including dermal fibroblasts in an appropriate ratio, and 1.0 mg/ml of a basement membrane component was further added thereto to obtain a mixed solution.

150 μl of each of the solutions thus obtained was placed in Example 1, and stored for 30 minutes in an incubator at 37° C. and 5% $CO_2$ and thus gelled.

Keratinocytes (Normal Human Epidermal Keratinocytes, LONZA) were seeded at 250,000 cells/$cm^2$ onto the dermis equivalent formed as described above, and a culture medium (Keratinocyte Growth Medium-GOLD, LONZA) was placed in the inner and outer chambers of the culture vessel, followed by cell attachment overnight. Thereafter, the culture medium was removed from the culture vessel, a culture medium for forming an epidermis was placed in the outer chamber, and differentiation of the keratinocytes was induced. Thereafter, the epidermis was formed by inducing differentiation for 10 days while changing the culture medium every day.

The reconstructed human skin that was finally produced after culture as described above was photographed, and the sliced reconstructed human skin was stained with hematoxylin and eosin (H&E) and observed using an optical microscope. The results thereof are shown in FIGS. 6A and 6B. FIG. 6A is images showing the reconstructed human skin produced according to Example 1, and FIG. 6B is an optical microscope image showing the histology of the reconstructed human skin produced according to Example 1 stained with hematoxylin and eosin (H&E).

Consequently, as shown in FIG. 6A, the culture vessel having the inner wall coated with dopamine in Example 1 according to the present invention created strong adhesion between the type-I-collagen-based three-dimensional hydrogel scaffold and the inner wall of the culture vessel, thereby preventing the matrix from being detached from the inner wall of the culture vessel due to internal tension generated by the dermal fibroblasts contained in the dermis equivalent or contractile force generated by the migratory epidermal keratinocytes during the differentiation thereof, confirming that no contraction occurred. In addition, it was confirmed that the reconstructed human skin produced according to Example 1 was structurally very similar to human skin as shown in FIG. 6B.

Experimental Example 4: Evaluation of Skin Barrier Function of Reconstructed Human Skin with Liquid Surfactant In order to confirm the skin barrier function of the reconstructed human skin produced according to the present invention, the skin barrier function was evaluated using the reconstructed human skin produced in the culture vessel having the inner wall coated with dopamine in Example 1. The skin barrier function was evaluated in a manner in which cell viability relative to an untreated control depending on the treatment time with 1% Triton X-100 was measured, and $ET_{50}$ (Effective Time 50%), which is the time taken to reach the cell viability of 50%, was determined, according to the barrier evaluation method presented as a performance standard in OECD Test Guideline 439.

The upper surface of the reconstructed human skin produced using Example 1 was treated with 200 μl of a 1% Triton X-100 solution and allowed to react for 2 hours, 5 hours, 8 hours, and 20 hours, followed by reaction with 1 mg/ml of an MTT solution for 3 hours along with an untreated control, whereby a thiazolyl blue formazan dye was formed through reaction with viable cells and photographed, and depending on the treatment time, the sliced reconstructed human skin was stained with hematoxylin and eosin (H&E) and observed using an optical microscope. The results thereof are shown in FIG. 7. The formazan dye thus formed was dissolved in 2 ml of 2-propanol, 200 μl thereof was placed in each of two wells of a 96-well plate, and optical density at a wavelength of 570 nm was measured using a plate reader, and each optical density of treated group was compared to those in untreated control, thereby calculating relative cell viability, and $ET_{50}$ (Effective Time 50), which is the time taken to reach the cell viability of 50%, was determined. The results thereof are shown in FIG. 8.

Consequently, as shown in FIG. 7, it was confirmed that the amount of the formazan dye formed by the MTT reaction decreased with an increase in the treatment time with 1% Triton X-100, and also that the epidermis of the reconstructed human skin was damaged and thus the structure thereof was broken, and damage occurred to the dermis under the epidermis.

In addition, as shown in FIG. 8, the relative viability decreased depending on the treatment time with 1% Triton X-100, and the $ET_{50}$ value was about 4.5 hours, confirming that the criteria of barrier property presented as a performance standard in OECD Test Guideline 439 were satisfied.

As is apparent from the above description, according to the present invention, the inside of a culture vessel for culturing reconstructed human skin is coated with dopamine, which is a bio-based component that exhibits strong adhesion, making it possible to solve problems due to detachment of a type-I-collagen-based three-dimensional hydrogel scaffold matrix from the inner wall of the culture vessel and to maintain physiological relevance of existing reconstructed human skin. Thereby, reconstructed human skin configured such that a mature reconstructed epidermis having a skin barrier function is formed on a dermis equivalent matrix can be produced without contraction. The reconstructed human skin thus produced is capable of delivering the treated liquid material to the inside of the reconstructed human skin through the epidermis having a skin barrier function from the upper portion of the reconstructed human skin.

An experimental method of evaluating the extent of cell death of skin tissue by topical application of a liquid surfactant onto the upper portion of reconstructed human skin is the most accurate and direct method of evaluating the skin barrier function of reconstructed human skin. For this method to be possible, there is a prerequisite that contraction of reconstructed human skin must not occur during formation of a mature epidermis having a skin barrier function. Since conventional methods of culturing reconstructed human skin do not satisfy the prerequisite, it is difficult to evaluate the barrier function, but an experiment of evaluating the barrier function of reconstructed human skin is enabled in the present invention.

In order to evaluate the toxicity of a specific component on the skin or the efficacy of a specific component in improvement of the function of the skin, there is a prerequisite that a sample containing the component has to be topically applied onto the outermost layer of the skin and delivered to the inside of the skin through the skin barrier. Therefore, thorough research into formulation technology for efficiently delivering the component into the skin is ongoing. However, in the case in which the upper portion of existing reconstructed human skin with contraction is treated with a sample, the sample is mixed with the culture medium through the porous membrane area exposed by contraction and is delivered directly into the dermis equivalent of the reconstructed human skin under the epidermis thereof, and as such, there is a limitation in that the skin barrier function of the epidermis is neglected. The present invention makes it possible to study the efficiency of a specific component in penetration of the skin barrier and in delivery into the skin.

Although the present invention has been described in detail through specific embodiments, these embodiments are intended to specify the present invention, and the present invention is not limited thereto, and it is obvious that modifications or improvements thereof are possible by those of ordinary skill in the art within the technical spirit of the present invention.

All simple modifications and variations of the present invention belong to the scope of the present invention, and the specific protection scope of the present invention will be made clear by the appended claims.

What is claimed is:

1. A method of producing reconstructed human skin using a culture vessel comprising an inner chamber surrounded by a vertical inner side wall and a porous bottom surface and an outer chamber spaced apart from the inner chamber and configured to surround the inner chamber, comprising:

preparing a coating solution by dissolving a dopamine in a powder form in a solvent;

forming an adhesive layer by coating and reacting the coating solution on a surface of the vertical inner side wall surrounding the inner chamber, and culturing the reconstructed human skin in the inner chamber in contact with the adhesive layer formed on the surface of the vertical inner side wall, wherein the dopamine in the coating solution is at a concentration of 0.1 to 20 mg/ml and the coating solution on the surface of the vertical inner side wall is allowed to react for 1 to 3 hours, and wherein the culturing the reconstructed human skin in the inner chamber comprises:

forming a three-dimensional hydrogel scaffold matrix by placing a scaffold solution comprising a type I collagen solution in the inner chamber and performing gelling; and seeding epidermal keratinocytes onto the three-dimensional hydrogel scaffold matrix, wherein the adhesive layer provides an adhesive force between the surface of the vertical inner side wall and the three-dimensional hydrogel scaffold matrix so as to prevent deformation and detachment of the three-dimensional hydrogel scaffold matrix due to mechanical stress generated during keratinocyte differentiation.

2. The method according to claim 1, wherein the solvent is Tris-HCl at a pH of 8.0 to 9.0.

3. The method according to claim 1, wherein the scaffold solution further comprises dermal fibroblasts.

4. The method according to claim 1, wherein the scaffold solution further comprises a basement membrane component material.

5. The method according to claim 1, wherein the seeding the epidermal keratinocytes comprises supplying a first culture medium comprising the epidermal keratinocytes to the inner chamber.

6. The method according to claim 1, further comprising supplying a first culture medium to the inner chamber and the outer chamber so that the epidermal keratinocytes are attached, after seeding the epidermal keratinocytes.

7. The method according to claim 5, further comprising removing the first culture medium and supplying a second culture medium to the outer chamber so that the epidermal keratinocytes differentiate.

* * * * *